(12) United States Patent
Ying et al.

(10) Patent No.: US 9,108,897 B2
(45) Date of Patent: Aug. 18, 2015

(54) METHOD FOR DESORBING AND REGENERATING BUTANOL-ADSORBING HYDROPHOBIC MACROPOROUS POLYMER ADSORBENT

(75) Inventors: Hanjie Ying, Nanjing (CN); Xiaoqing Lin, Nanjing (CN); Jiansheng Fan, Nanjing (CN); Jinglan Wu, Nanjing (CN); Yong Chen, Nanjing (CN); Xiaochun Chen, Nanjing (CN); Jingjing Xie, Nanjing (CN); Jian Xiong, Nanjing (CN); Jianxin Bai, Nanjing (CN)

(73) Assignee: Nanjing University of Technology, Jiangsu (CN)

( * ) Notice: Subject to any disclaimer, the term of this patent is extended or adjusted under 35 U.S.C. 154(b) by 0 days.

(21) Appl. No.: 14/130,887

(22) PCT Filed: Jul. 5, 2011

(86) PCT No.: PCT/CN2011/076876
§ 371 (c)(1),
(2), (4) Date: Jan. 3, 2014

(87) PCT Pub. No.: WO2013/004009
PCT Pub. Date: Jan. 10, 2013

(65) Prior Publication Data
US 2014/0155658 A1 Jun. 5, 2014

(51) Int. Cl.
*B01J 38/48* (2006.01)
*C07C 29/76* (2006.01)
*B01D 15/20* (2006.01)
*B01J 20/34* (2006.01)
*B01D 15/42* (2006.01)

(52) U.S. Cl.
CPC .............. *C07C 29/76* (2013.01); *B01D 15/203* (2013.01); *B01J 20/3425* (2013.01); *B01J 20/3475* (2013.01); *B01D 15/426* (2013.01)

(58) Field of Classification Search
CPC ........................................................ B01J 38/48
USPC ................................................. 502/22, 29, 33
See application file for complete search history.

(56) References Cited

FOREIGN PATENT DOCUMENTS

| CN | 101524488 A | 9/2009 |
|---|---|---|
| CN | 101805754 A | 8/2010 |
| WO | WO2008/095896 A1 | 8/2008 |
| WO | WO 2008095896 A1 * | 8/2008 |

OTHER PUBLICATIONS

Nielsen, David R., et al., In Situ Product Recovery of n-Butanol Using Polymeric Resins, Biotechnology and Bioengineering, vol. 102, No. 3, Feb. 15, 2009, 11 pages.

* cited by examiner

*Primary Examiner* — Edward Johnson
(74) *Attorney, Agent, or Firm* — Christie, Parker & Hale, LLP

(57) ABSTRACT

The present invention provides a method for desorbing and regenerating a butanol-adsorbing hydrophobic macroporous polymer adsorbent, comprising: successively eluting the hydrophobic macroporous polymer adsorbent with butanol adsorbed therein using a water soluble low-boiling-point polar solvent and water. The method provided in the present invention has a simple process, a short separation time, easy, fast and complete desorption and regeneration, low equipment investment and pollution, and reduced energy consumption, and therefore production is easy on a large scale.

15 Claims, 3 Drawing Sheets

METHOD FOR DESORBING AND REGENERATING BUTANOL-ADSORBING HYDROPHOBIC MACROPOROUS POLYMER ADSORBENT

CROSS-REFERENCE TO RELATED APPLICATION(S)

This application is a National Phase Patent Application and claims priority to and benefit of International Application Number PCT/CN2011/076876, filed on Jul. 5, 2011, the entire disclosure of which is incorporated herein by reference.

TECHNICAL FIELD

The present invention relates to a method for desorbing and regenerating a butanol-adsorbing resin, especially to a method for desorbing and regenerating a resin with butanol fermentation broth adsorbed therein, and belongs to the technical field of the extraction and purification.

BACKGROUND

Diversification of the country's energy supply is an important aspect of the national energy policy, and the renewable bioenergy will be one of the main energy sources for use in the world's future energy structure. As a new biofuel, butanol has huge market potential with the perfection of upstream and downstream engineering technology for acetone-butanol fermentation industry.

Butanol (n-butanol and 1-butanol) is a four-carbon primary alcohol, with molecular formula of $C_4H_9OH$ and molecular weight of 74.12. Butanol is a colorless liquid with a distinct odor, and its vapor exerts an irritative effect on mucous membranes and has anesthetic effects at high concentrations. Butanol is mainly used for manufacture of plasticizers such as dibutyl phthalate and aliphatic dibasic acid butyl ester, and is widely used for manufacture of a variety of plastic and rubber products. Butanol can also be used to produce butyraldehyde, butyric acid, butylamine and butyl acetate, which can be used as solvents of resins, paints and adhesives and can also be used as extractants of oils and fats, drugs and spices and additives of alkyd resin paints. In addition, butanol is also a new biofuel with tremendous potential.

However, there are still many problems with the traditional butanol fermentation industries in terms of large-scale industrial application. Wherein a key problem is the low final concentration of the solvent in the fermentation broth. In the ordinary biological methods for preparing butanol, since butanol has toxic effects on bacteria, the mass concentration of butanol is less than 13 g/L, and the yield of butanol is less than 0.29 g/(L·h), and the output of butanol is less than 25% (by mass), resulting in the total mass percent of the solvent in the fermentation broth less than or equal to 2% accordingly. In order to obtain commercial butanol, it is required to use conventional distillation methods, leading to consumption of large quantities of energy.

In order to solve this critical problem, it is necessary to remove the products of ABE (acetone-butanol-ethanol) from the fermentation broth with an effective method, so as to reduce inhibition on product, thereby enhancing fermentation yield and reducing industrial costs.

Currently, the main techniques for separating fermentation products of ABE include gas stripping (GS), liquid-liquid extraction, pervaporation (PV) and adsorption. Meagher (U.S. Pat. No. 5,755,967) et al. separate acetone and butanol by developing a zeolite membrane filled with silicone rubber according to the pervaporation method. The zeolite membrane has excellent selective adsorption on acetone and butanol relative to the adsorption of ethanol, acetic acid and butyric acid. This patent also reports the thermal analytical method, in which the silicalite is heated to 78° C., and the recovery rate of butanol, acetone and ethanol are 100%, 95.5% and 80% respectively, but there are not reports related to test on solubility of ABE in the elution phase. Qureshi, N. et al. (Qureshi, N. et al, 2005, Bioprocess and Biosystems Engineering, 27(4):215-222) recover biobutanol by the adsorption-desorption method, which is the best recovery process when it comes to energy consumption. DIJK (WO 2008/095896 A1) et al. separate biobutanol using a microporous resin with ultra-high crosslinking degree, however the resin has a certain adsorption capacity for ethanol and acetone, increasing the cost of post-separation process. Arjan Oudshoorn et al. (Arjan Oudshoorn et al, 2009, Biochemical Engineering Journal, 48:99-103) adsorb and separate biobutanol by using a zeolite, and investigate adsorption properties of three zeolites (that is, BV28014, CBV811, CBV901) on biobutanol, however, there are problems that the adsorption capacity of the zeolite on biobutanol is not high and the zeolite also adsorbs acetone and ethanol while adsorbing butanol, resulting in increased cost on separation in later stage. David R. Nielsen et al. (David R. Nielsen et al, 2009, Biotechnology and Bioengineering, 102(3):811-821) recover biobutanol in-situ using a polymer resin and investigate the adsorption property of the polymer resin on biobutanol, but there exists following problems: the resin contacts with the fermentation broth directly, resulting in pollution of the resin; the biocompatibilities of some resins are not good; some resins can absorb the substrate of glucose and fermentation reaction intermediates; the adsorption capacities of some resins are low; although some resins have high adsorption capacity on butanol, they also adsorb a great deal of acetone, ethanol and other substances. Milestone et al. (Milestone, N. B. et al, 1981, J Chem Technol Biotechnol, 31:732-736) desorb butanol from the siliceous rock according to the thermal desorption method in which the siliceous rock is first heated to 40° C. to remove water from the siliceous rock, and then heated to 150° C. to recover butanol with the concentration of butanol in the eluent reaching 790-810 g/L, however, it does not involve report on problems of butanol recovery rate and regeneration method. Das et al. (Das, K. et al, 1987, In: Proceedings 4th European congress on biotechnol, 1: 76-78) realize butanol recovery rate of 60-65%, 75-85% and 75-85% respectively by using 120° C. heated steam through the activated carbon, IRC-50 resin bed and XAD-2 resin bed, wherein the outlet gas is condensed using 0° C. water. In summary, there usually exists two main problems with the current adsorbents for butanol fermentation broth: firstly, the absorption capacity of the adsorbent is low, for example, the absorption capacity is less than 100 mg butanol/g adsorbent; secondly, butanol cannot be desorbed from the adsorbent effectively, resulting in lower overall recovery rate of butanol.

SUMMARY

The first technical problem to be solved by the present invention is: in the prior art, the adsorption capacity of the adsorbent for adsorbing butanol fermentation broth is not high, and the washing solvent used in the desorption method cannot effectively implement dissolving and removing of butanol and other substances in the adsorbent, therefore it is needed to provide a desorption and regeneration method where butanol and other substances in the adsorbent (such as resin) with butanol fermentation broth adsorbed therein can be dissolved effectively and thoroughly through a suitable washing solvent.

The second technical problem to be solved by the present invention is: in the prior art, the adsorbent needs to be taken out from a adsorption-desorption column during regeneration of the resin with butanol fermentation broth adsorbed therein and then loaded into the adsorption-desorption column after regeneration, resulting to in consumption of time and low production efficiency, therefore it is needed to provide a regeneration method suitable for large-scale industrial production where the resin with saturated adsorption of butanol fermentation broth therein can be desorbed directly without taking it out from the adsorption-desorption column.

The third technical problem to be solved by the present invention is: it is needed to consume large quantities of solutions such as organic solvent, acid and base during the regeneration of adsorbents in the prior art, leading to serious pollution and high cost, therefore it is needed to provide a regeneration method where the fixed-bed is eluted with water directly after desorption of the resin with butanol fermentation broth adsorbed therein in the adsorption-desorption column directly to recover the adsorption property of the resin.

In order to solve the above problems, the object of the present invention is to provide a method for desorbing and regenerating a butanol-adsorbing adsorbent to recover butanol and regenerate the adsorbent economically and effectively.

The object of the present invention is implemented by the following technical solution.

In one aspect, the present invention provides a method for desorbing and regenerating a butanol-adsorbing hydrophobic macroporous polymer adsorbent, the method comprises: eluting a hydrophobic macroporous polymer adsorbent with butanol adsorbed therein using a water soluble low-boiling-point polar solvent and water successively. Wherein butanol in the hydrophobic macroporous polymer adsorbent can be desorbed by the water soluble low-boiling-point polar solvent, and then the residual water soluble low-boiling-point polar solvent can be removed by eluting with water, so that the hydrophobic macroporous polymer adsorbent with butanol adsorbed therein can be desorbed and regenerated so as to be continually used for the adsorption of butanol.

Wherein the hydrophobic macroporous polymer adsorbent with butanol adsorbed therein may be a hydrophobic macroporous polymer adsorbent with butanol fermentation broth adsorbed therein, that is, butanol is adsorbed by adsorption of the butanol fermentation broth. The adsorption may be saturated adsorption or may be adsorbed to a certain extent.

Preferably, the method may further comprise: eluting the hydrophobic macroporous polymer adsorbent with water before eluting it with the water soluble low-boiling-point polar solvent. Preferably, eluting the hydrophobic macroporous polymer adsorbent with water is performed at room temperature, preferably 20-25° C., wherein water for elution is used in an amount of 1-2 bed volumes and at a flow rate of 0.5-0.8 bed volumes/hour. In the case that the hydrophobic macroporous polymer adsorbent adsorbs butanol fermentation broth, the residual butanol fermentation broth which is not adsorbed by the adsorbent or some impurities in the fermentation broth can be washed off by this operation.

Preferably, the adsorbent used in the method is a non-polar and/or weak-polar hydrophobic macroporous polymer adsorbent; more preferably, the non-polar hydrophobic macroporous polymer adsorbent has a skeleton of styrene diethylbenzene; the weak-polar hydrophobic macroporous polymer adsorbent has a skeleton of polyacrylamide or styrene diethylbenzene, and has a polar functional group containing nitrogen, oxygen or sulfur.

The adsorbent used in the present invention may comprise the following performances:

the inner surface of the hydrophobic macroporous polymer adsorbent is 100-2000 $m^2/g$;

the particle size of the hydrophobic macroporous polymer adsorbent is 20-60 mesh;

the pore diameter of the hydrophobic macroporous polymer adsorbent is 1-180 nm;

the pore volume of the hydrophobic macroporous polymer adsorbent is 0.4-3 $cm^3/g$;

the wet apparent density of the hydrophobic macroporous polymer adsorbent is 590-750 g/L;

the water-containing content of the hydrophobic macroporous polymer adsorbent is 40-80%.

In a preferred embodiment of the present invention, butanol is separated by using the following two hydrophobic macroporous resins: one is a non-polar resin, which has a skeleton structure of styrene diethylbenzene without any functional groups, and exerts hydrophobic effect (that is, hydrophobic force) mainly depending on the n-alkyl side chain of butanol and the benzene ring of the skeleton of styrene diethylbenzene; the other is a weak-polar resin, which has a skeleton of polyacrylamide or styrene diethylbenzene and generally has polar functional groups containing nitrogen, oxygen or sulfur such as an amide, cyano or phenolic hydroxyl group, and generates hydrogen bonding force mainly depending on the alcohol hydroxyl group of butanol and the hydroxyl group of the polar functional group in the polar adsorption resin. After the hydrophobic macroporous resin adsorbs the butanol fermentation broth to achieve saturation, the residual unabsorbed liquid is first washed off with water, and then butanol is desorbed from the adsorbent to regenerate the adsorbent according to the desorption and regeneration method of the present invention.

Butanol or butanol fermentation broth is adsorbed by the hydrophobic macroporous polymer adsorbent at a temperature of 10-37° C., preferably 30-37° C. The initial concentration of butanol in the butanol fermentation broth containing butanol is 5-400 g/L.

Furthermore, the butanol used in the method of the present invention is preferably n-butanol.

Preferably, the water soluble low-boiling-point polar solvent used in the method is lower alcohol, ketone, ether, ethyl benzene or ethyl acetate, or a mixture of any two or more solvents selected from the group consisting of lower alcohol, ketone, ether, ethyl benzene and ethyl acetate in any proportion, or a mixture of water with any one or more solvents selected from the group consisting of lower alcohol, ketone, ether, ethyl benzene and ethyl acetate in any proportion;

more preferably, the water soluble low-boiling-point polar solvent is methanol, ethanol, propanol, acetone, ethyl acetate or ethyl benzene, or a mixture of any two or more solvents selected from the group consisting of methanol, ethanol, propanol, acetone, ethyl acetate and ethyl benzene in any proportion, or a mixture of water with any one or more solvents selected from the group consisting of methanol, ethanol, propanol, acetone, ethyl acetate and ethyl benzene in any proportion.

Preferably, in the method, the hydrophobic macroporous polymer adsorbent is eluted with the water soluble low-boiling-point polar solvent at a flow rate of 0.5-10 bed volumes/hour, more preferably 0.6-1.5 bed volumes/hour and in amount of 0.5-10 bed volumes, more preferably 1-4 bed volumes. Moreover, the elution temperature is preferably 10-50° C.; more preferably, the desorption temperature is 20-40° C.

Furthermore, after being eluted with the water soluble low-boiling-point polar solvent, the hydrophobic macroporous polymer adsorbent is eluted with water in amount of 1-2 bed volumes and at a water flow rate of 0.5-1 bed volumes/hour at room temperature.

According to specific embodiments of the present invention, the specific process of the desorption and regeneration method in the present invention may include: first, adsorbing the butanol fermentation broth by a hydrophobic macroporous polymer adsorption resin column to a certain extent (e.g., achieving saturation), then eluting the adsorption bed with a washing agent (water) to remove the unabsorbed fermentation broth at the surface of or in the pore channels of the adsorbents, and draining the washing agent in the adsorption bed, then adding a certain volume of desorbent (i.e. the water soluble low-boiling-point polar solvent of the present invention), and infiltrating for 5 min first, and then desorbing the butanol in the resin phase by the desorbent, and finally eluting the desorbed bed with a regenerate (water) until there is no desorbent in the effluent, then the regeneration is completed, and the next stage of adsorption-desorption operation can be carried out.

The butanol-containing effluent obtained by the desorption and regeneration method of the present invention mainly contains desorbent, butanol and so on, the desorbent with low-boiling-point can be first distilled by distillation to be recycled, and then butanol is distilled at elevated temperature, so that butanol can be obtained by recovery.

Butanol is a hydrophobic and volatile substance, which generates adsorption force mainly by van der Waals forces and hydrogen bond to combine with the adsorbent. In the desorption and regeneration method of the present invention, a water soluble low-boiling-point polar organic solvent is selected to wash the saturated adsorption resin, wherein the polar solvent is selected based on the principle of "like dissolves like", then butanol and other substances in the saturated adsorption resin are dissolved by washing with a polar organic solvent; a water soluble solvent is selected based on the fact that the water solubility of the solvent enables the residual eluent within the adsorption resin after elution to be easily taken out by water; and use of a low-boiling-point solvent enables the solvent to be recovered easily by distillation; and a polar solvent is selected based on the fact that it not only can dissolve butanol, but also can swell the hydrophobic macroporous adsorption resin so that the adsorption force between the adsorbent and solute (i.e. butanol) can be weakened. Furthermore, different adsorbents have different skeleton structures and functional groups, resulting in different hydrophobic force between the resin and butanol, which affects the adsorption and desorption of the resin. The desorption rate of the hydrophobic macroporous polymer adsorbent obtained by screening in the present invention can reach above 99.3%, while the highest desorption rate of the resin reported is only 85%.

In summary, the main advantages of the present invention are as follows:

(1) a special L-15 resin is used to adsorb butanol in the present invention, the experiments prove that the absorption capacity of the resin on butanol is very high with no by-products such as acetone and ethanol adsorbed.

(2) in the method for desorbing and regenerating a butanol-adsorbing hydrophobic macroporous polymer adsorbent of the present invention, by using a water soluble low-boiling-point polar solvent such as lower alcohol, ketone, ether, ethyl benzene, ethyl acetate, or the mixed solution of the above substances in any proportion, or the mixed solution of the above substance(s) with water in any proportion, fully dissolution and removal of butanol and other substances adsorbed inside the adsorbent (e.g. saturated adsorption resin) can be realized, and the desorbent can be recovered by distillation to be recycled; in addition, by elution of the residual desorbent inside the adsorbent with water, the processing of the residual desorbent in the resin can be realized, and therefore the adsorbent is regenerated.

(3) in the method for desorbing and regenerating a butanol-adsorbing hydrophobic macroporous polymer adsorbent of the present invention, the desorption and regeneration of the adsorbent (such as butanol-adsorbing resin) can be carried out directly in the butanol-adsorbing adsorption-desorption column without taking out the adsorbent from the adsorption-desorption column, saving a great deal of time and improving the regeneration efficiency.

(4) in the desorption and regeneration method of the present invention, the desorbed bed is eluted with water to recover the adsorption property of the resin, saving large quantities of solutions such as organic solvent, acid and base, with little pollution and low cost, and also saving a lot of time and improving the regeneration efficiency.

A water soluble low-boiling-point polar organic solvent is used to desorb butanol from the adsorbent more effectively, and a small amount of 2-3 bed volumes of water is used to regenerate the adsorbent, and according to the difference in affinities of the macroporous polymer adsorbent on the target substance of butanol and on the impurities such as acetone and ethanol, a hydrophobic macroporous polymer adsorbent with functional groups only adsorbing butanol but not adsorbing/adsorbing little acetone and ethanol is used to further achieve efficient separation of butanol from acetone and ethanol. Thus it can be seen that, the method of the present invention is novel and advantaged in simple process, short separation time, high recovery efficiency of butanol, easy, fast and complete desorption and regeneration, low investment in equipment and production costs, little pollution, reduced energy consumption, and is therefore easy for scale production with great promotion prospects. Experiments show that, with the method of the present invention, the yield of butanol can reach up to 99.8% and the adsorption capacity of the hydrophobic macroporous adsorption resin on butanol keeps basically unchanged through 30 cycles.

BRIEF DESCRIPTION OF THE DRAWINGS

Hereinafter, the embodiments of the present invention will be described in detail in combination with the accompanying drawings, wherein.

DETAILED DESCRIPTION OF THE EMBODIMENTS

Figure 1:
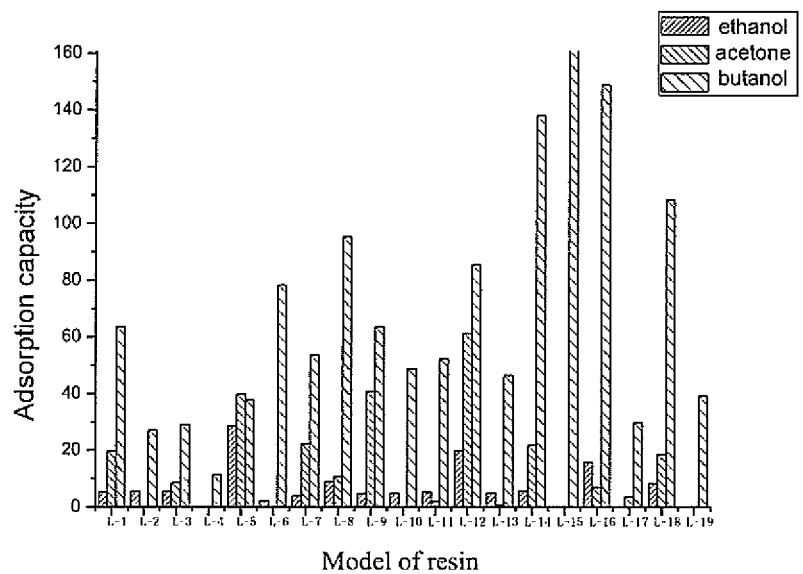
FIG. 1 shows results of adsorption capacities of various macroporous adsorption resins measured in Example 1 of the present invention.

The present invention will be described with reference to specific examples. Those skilled in the art will appreciate that these examples are only intended to illustrate the present invention, rather than limit the scope of the present invention in any way.

The experimental methods in the following examples are all conventional methods unless expressly stated; and the experimental materials used in the examples were all purchased from conventional biochemical reagents store unless expressly stated. In the examples, the concentrations of the mixed solution (ABE) containing acetone, butanol and ethanol are detected by gas phase chromatography, and the instruments and conditions for measurement are as follows:

Agilent 7890 gas chromatography, HP-INNOWAX (19091N-236) capillary chromatography column (60 m×0.251 mm×0.50 μm).

Temperature programming: keeping at the initial temperature of 70° C. for 1 min, and then increasing the temperature to 190° C. at the rate of 20° C./min, and keeping at 190° C. for 2 min, with the total running time of 9 min.

Total flow is 100 mL/min, the flow rate of the carrier gas ($N_2$) is 90 mL/min; the column flow is 1 mL/min; the flow rate of $H_2$ is 30 mL/min; and the flow rate of air is 300 mL/min.

Temperature of the injection port is 180° C., temperature of FID detector is 220° C., injection volume is 1.0 μL, and split ratio is 90:1.

Quantitative analysis is performed by the internal standard method, and the internal standard is isobutanol.

In the following examples, the adsorption capacity of the macroporous adsorption resin is calculated according to the following formula:

$$q_e = \frac{(C_0 - C_e)V}{W}$$

wherein, $C_0$ represents the initial solubility (g/L) of butanol; $C_e$ represents the balanced solubility (g/L) of butanol; V represents the volume (L) of the butanol-containing solution; and W represents the mass (g) of the macroporous polymer adsorbent.

After adsorption equilibrium is reached, the residual adsorption solution is removed, and the saturated adsorption resin is desorbed by a water soluble low-boiling-point polar organic solvent, the desorption rate of the resin (i.e. desorption rate of butanol) is calculated according to the following formula:

$$D\% = C_x V_2 / (C_0 - C_e) V_1$$

wherein, $C_x$ represents the concentration (g/L) of butanol in the desorption solution after completion of desorption, $V_2$ represents the volume (L) of the desorption solution; and $V_1$ represents the total volume (L) of the absorption solution.

Example 1

In the present example, the adsorption capacities of different hydrophobic macroporous polymer adsorbents on acetone, butanol and ethanol in the mixed solution were measured, and the specific process was as follows.

A certain concentration of ABE mixed solution was prepared, wherein the concentration of butanol is 15 g/L, and the mass ratio of acetone, butanol and ethanol is 3:6:1, that is, the mass concentration of the three components in ABE is 3:6:1. 1 g macroporous polymer adsorbent ($L_{1-19}$ shown in FIG. 1, which are respectively Amberlite series resins, Diaion series resins and D series resins) dried by suction was added into the above ABE mixed solution respectively, after saturated absorption is reached, the adsorption capacities and separation factors of the macroporous polymer adsorbents on ABE are calculated according to the GC method.

Results of separation factors are shown in Table 1.

TABLE 1

| Model of resins | $\alpha_{ethanol}^{butanol}$ | $\alpha_{acetone}^{butanol}$ |
|---|---|---|
| L-1 | 2.31 | 1.59 |
| L-2 | 0.89 | 35.6 |
| L-3 | 0.95 | 1.67 |
| L-4 | 8.33 | 14.56 |
| L-5 | 0.20 | 0.42 |
| L-6 | 7.22 | 110.83 |
| L-7 | 2.73 | 1.17 |
| L-8 | 2.10 | 4.80 |
| L-9 | 2.68 | 0.72 |
| L-10 | 1.89 | 66.19 |
| L-11 | 1.89 | 13.54 |
| L-12 | 0.76 | 0.62 |
| L-13 | 1.75 | 33.57 |
| L-14 | 5.19 | 3.49 |
| L-15 | 943.51 | 297.93 |
| L-16 | 2.02 | 12.79 |
| L-17 | 124.18 | 4.03 |
| L-18 | 2.66 | 3.09 |
| L-19 | 165.48 | 52.25 |

The experimental results of adsorption capacities are shown in FIG. 1. As can be seen from FIG. 1, Diaion series resins (L-2, L-3, L-4, L-13, L-17) have relatively small adsorption capacity of butanol, and L-17 resin also adsorbs a small amount of byproducts such as acetone while adsorbing butanol; D series resins (L-1, L-5, L-6, L-7, L-8, L-9, L-10, L-11, L-12, L-14, L-16, L-18) have a slightly higher adsorption capacity of butanol, but they also absorb byproducts such as acetone and ethanol; Amberlite series resins (L-15, L-19) have a very high adsorption capacity of butanol, and they do not absorb byproducts such as acetone and ethanol. Wherein L-15 resin is a weak-polarity hydrophobic macroporous polymer adsorbent, which has a skeleton of styrene diethylbenzene and is an adsorption resin which has polar functional groups containing nitrogen, oxygen, sulfur, such as amide, cyano, phenolic hydroxyl group.

Methods for measuring various parameter of the resin are as follows:

The water content of the resin is measured according to the method disclosed in the literature (GB5757-86[S]); the content of active groups and apparent density ($r_a$) of the resin are measured by referring to the method disclosed in the literature (Binglin H E, Wenqiang Huang, Ion exchange and adsorption resin [M]. Shanghai: Shanghai Scientific and Technological Education Press, 1995); the specific surface area of the resin is measured by referring to the method disclosed in the literature (Qiming Tan, Zuoqing Shi, Measuring specific surface of porous resin with simple nitrogen adsorption method[J]. Ion Exchange and Adsorption, 1987, 3(1):30) through a simple BET instrument; the pore volume ($V_{pore\ volume}$) is calculated according to the formula $V_{pore\ volume} = 1/r_T$; and the average pore diameter is calculated according to the formula $r = 2V_{pore\ volume}/S$.

Example 2

Figure 3:
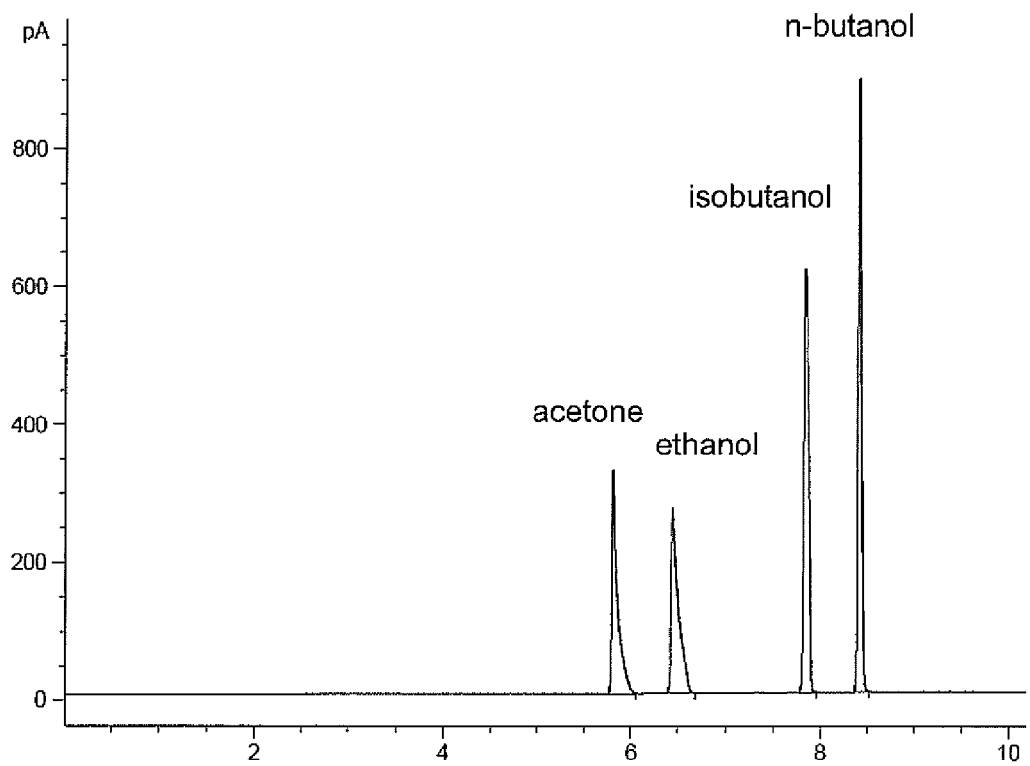
FIG. 3 shows a GC chromatogram of supernatant in the broth after 48 hours of anaerobic fermentation with *Clostridium acetobutylicum*, wherein isobutanol is used as the internal standard.

In the present example, dynamic column adsorption was carried out using the L-15 macroporous adsorption resin (50 g) in Example 1, wherein the used butanol fermentation broth containing acetone, butanol and ethanol, was prepared as follows:

Anaerobic fermentation (nitrogen was bubbled into the fermentor before fermentation to maintain anaerobic environment, and the temperature was kept at 37° C.) was carried out using *Clostridium acetobutylicum* strain (provided by State Key Laboratory of Materials-Oriented Chemical Engineering, Nanjing University of Technology) according to the conventional method in the art, and the fermentation broth was obtained after 48 hours, and then the supernatant (GC chromatogram is shown in FIG. 3) was obtained through centrifugation, the measurements show that the supernatant of the fermentation broth contains 4.56 g/L acetone, 11.91 g/L butanol, 1.40 g/L ethanol, 0.60 g/L butyric acid, 0.80 g/L acetic acid and 10.0 g/L glucose. The supernatant of this fermentation broth is used as the butanol fermentation broth for experiments in this and the following examples.

Figure 2:
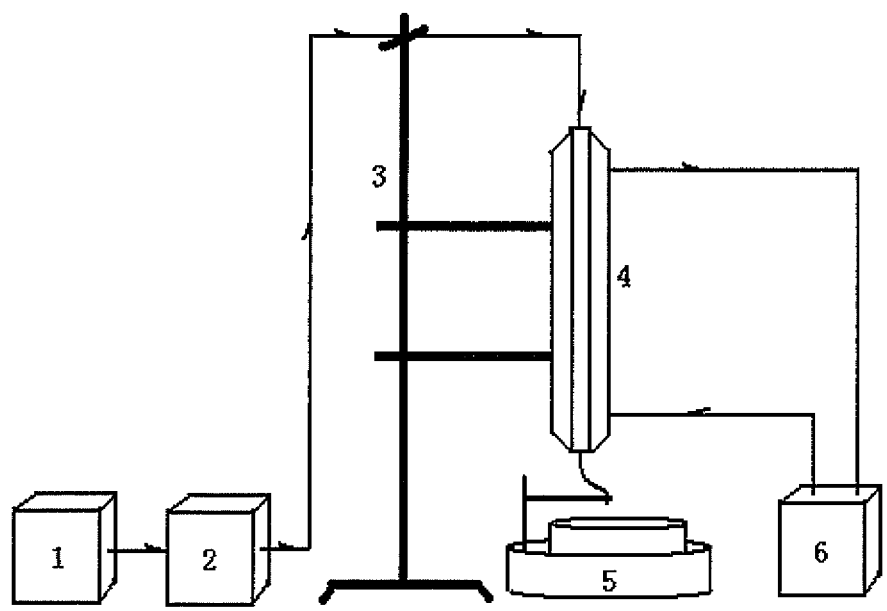
FIG. 2 shows the adsorption-desorption apparatus used in the examples of the present invention.
Figure 4:
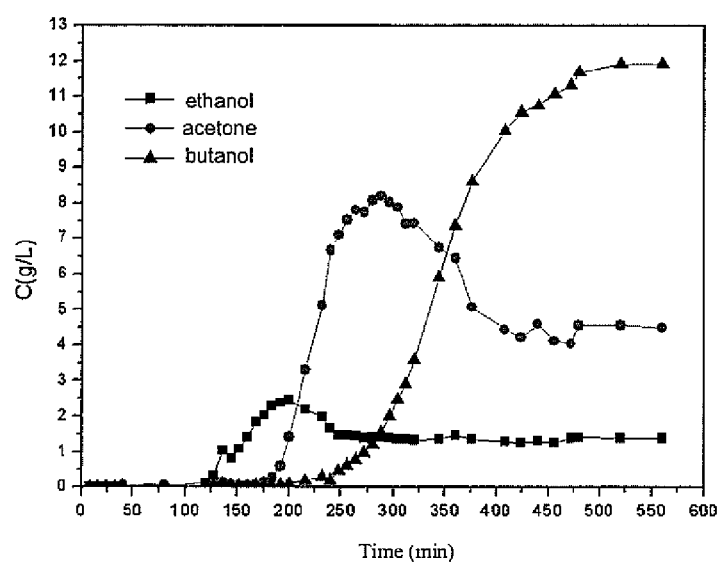
FIG. 4 shows an outflow curve measured at the outlet of the resin column after butanol fermentation broth is adsorbed according to Example 2 of the present invention.
Figure 5:
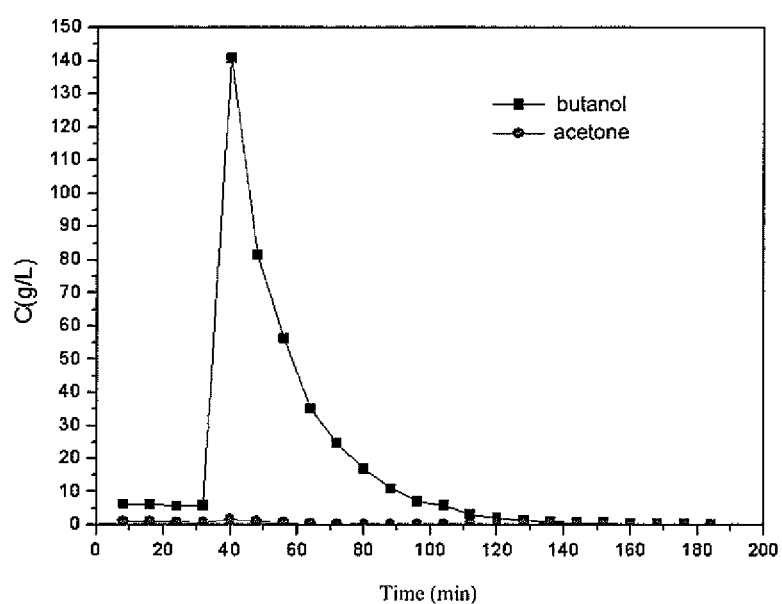
FIG. 5 shows a desorption curve measured at the outlet of the resin column during desorption of butanol adsorbed by the resin column according to Example 2 of the present invention.

Dynamic adsorption of the supernatant of the butanol fermentation broth above was carried out by using the experiment apparatus shown in FIG. 2, which specifically includes:

1) 1 L butanol fermentation broth containing acetone, butanol and ethanol was input into an adsorption-desorption column at a certain flow rate using a peristaltic pump. At the outlet of the column, samples were taken at regular time and the concentrations of acetone, butanol and ethanol were measured to obtain outflow curves (shown in FIG. 4);

2) after 10 hours, the unabsorbed fermentation broth at the surface of the adsorbent or in the pore channels of the adsorbent was washed with no less than 1 times the amount of resin (V/V) and then water was emptied from the absorbed bed;

3) a certain volume of methanol was added as a desorbent, and infiltration was first carried out for 5 min, and then butanol in the resin phase was desorbed, samples were taken at regular time at the outlet of the column and the concentrations of the target substances were measured to obtain the desorption curves (shown in FIG. 5);

4) finally, the desorbed bed was eluted with the regenerant (water) until there is no desorbent of methanol in the effluent, then the regeneration is completed, and the next stage of adsorption-desorption operation can be carried out.

It is proved through the above experiment that, L-15 resin can effectively adsorb butanol, and butanol can be effectively desorbed from L-15 resin with butanol adsorbed therein by using a water soluble low-boiling-point polar solvent of methanol.

Example 3

50 g L-15 resin was packed into a fixed bed, 1 L butanol fermentation broth (containing 4.56 g/L acetone, 11.91 g/L butanol, 1.40 g/L ethanol, 0.60 g/L butyric acid, 0.80 g/L acetic acid, 10.0 g/L glucose) was passed through the L-15 resin fixed bed at a flow rate of 1 BV/h, after 10 hours, measurements show that the volume of the remaining adsorption solution is 0.96 L, and the remaining adsorption solution contains 4.26 g/L acetone, 3.88 g/L butanol, 1.30 g/L ethanol, 0.56 g/L butyric acid, 0.72 g/L acetic acid and 9.6 g/L glucose.

The adsorption bed was washed with 2 BV water (until drying up), measurements show that the volume of the washing liquid is 0.2 L and the washing liquid contains 1.60 g/L acetone, 10.93 g/L butanol, 0.76 g/L ethanol, 0.312 g/L butyric acid, 0.294 g/L acetic acid and 3.92 g/L glucose. According to the mass conservation principle of each component, the saturated adsorption capacity of per gram of resin on each component calculated according to the following formula $$q_e = \frac{(C_0 - C_e)V}{W}$$

is: acetone 3 mg, butanol 120 mg, ethanol 0 mg, butyric acid 1 mg, acetic acid 0 mg, glucose 0 mg.

At 20° C., 1 BV methanol aqueous solution (85% V/V) was passed through the L-15 resin fixed bed with saturated adsorption of butanol fermentation broth at a flow rate of 0.6 BV/h to perform desorption. The volume of the elution effluent is 0.098 L, and the measurements show that the effluent contains 1.53 g/L acetone, 61.1 g/L butanol, 0.51 g/L butyric acid. Wherein the concentration of butanol in the eluent is 5.13 times the concentration of butanol in the fermentation broth.

The desorption rate of butanol is calculated to be 99.8% according to the formula $$D\% = C_x V_2 / (C_0 - C_e) V_1.$$

Methanol with low-boiling-point point was first distilled off by atmospheric rectification of the elution effluent, with recovery rate reaching 97.6%, and the resulting methanol can enter into the desorption liquid of next elution process; and then high concentration of butanol can be obtained by increasing temperature to above 120° C. under normal pressure or by reduced pressure distillation.

Example 4

At 20° C., 2 BV methanol aqueous solution (85% V/V) was passed through 50 g L-15 resin fixed bed with saturated adsorption of butanol fermentation broth at a flow rate of 1 BV/h.

When measurements show that there was no butanol in the desorption effluent, the remaining desorption solution was emptied from the bed, and 2 BV water was passed through the L-15 resin fixed bed at a flow rate of 0.6 BV/h.

According to the operation of Example 3, the amount of butanol in the desorption effluent was detected by GC, it is obtained through calculation that the desorption rate of butanol in the L-15 resin is 99.4%.

Example 5

At 20° C., 2 BV methanol aqueous solution (85% V/V) was passed through 50 g L-15 resin fixed bed with saturated adsorption of butanol fermentation broth at a flow rate of 0.8 BV/h to perform desorption of the resin.

When measurements show that there was no butanol in the desorption effluent, the remaining desorption solution was emptied from the bed, and 2 BV water was passed through the L-15 resin fixed bed at a flow rate of 0.6 BV/h.

According to the operation of Example 3, the amount of butanol in the desorption effluent was detected by GC, it is obtained through calculation that the desorption rate of butanol in the L-15 resin is 99.7%.

Example 6

At 40° C., 2 BV methanol aqueous solution (85% V/V) was passed through 50 g L-15 resin fixed bed with saturated adsorption of butanol fermentation broth at a flow rate of 1.2 BV/h to perform desorption of the resin.

When measurements show that there was no butanol in the desorption effluent, the remaining desorption solution was emptied from the bed, and 1 BV water was passed through the L-15 resin fixed bed at a flow rate of 0.5 BV/h.

According to the operation of Example 3, the amount of butanol in the desorption effluent was detected by GC, it is obtained through calculation that the desorption rate of butanol in the L-15 resin is 99.1%.

Example 7

At 30° C., 2 BV ethanol was passed through 50 g L-15 resin fixed bed with saturated adsorption of butanol fermentation broth at a flow rate of 0.8 BV/h to perform desorption of the resin.

When measurements show that there was no butanol in the desorption effluent, the remaining desorption solution was emptied from the bed, and 2 BV water was passed through the L-15 resin fixed bed at a flow rate of 0.8 BV/h.

According to the operation of Example 3, the amount of butanol in the desorption effluent was detected by GC, it is obtained through calculation that the desorption rate of butanol in the L-15 resin is 99.3%.

Example 8

At 30° C., 2 BV mixed solution of water, methanol and ethanol (water:methanol:ethanol=1:16:3 (volume ratio)) was passed through 50 g L-15 resin fixed bed with saturated adsorption of butanol fermentation broth at a flow rate of 1 BV/h to perform desorption of the resin.

When measurements show that there was no butanol in the desorption effluent, the remaining desorption solution was emptied from the bed, and 2 BV water was passed through the L-15 resin fixed bed at a flow rate of 0.8 BV/h.

According to the operation of Example 3, the amount of butanol in the desorption effluent was detected by GC, it is obtained through calculation that the desorption rate of butanol in the L-15 resin is 99.4%.

Example 9

At 30° C., 2 BV mixed solution of methanol and ethanol (methanol:ethanol=1:1 (volume ratio)) was passed through 50 g L-15 resin fixed bed with saturated adsorption of butanol fermentation broth at a flow rate of 1 BV/h to perform desorption of the resin.

When measurements show that there was no butanol in the desorption effluent, the remaining desorption solution was emptied from the bed, and 2 BV water was passed through the L-15 resin fixed bed at a flow rate of 0.5 BV/h.

According to the operation of Example 3, the amount of butanol in the desorption effluent was detected by GC, it is obtained through calculation that the desorption rate of butanol in the L-15 resin is 99.4%.

Example 10

At 30° C., 4 BV propanol was passed through 100 g L-15 resin fixed bed with saturated adsorption of butanol fermentation broth at a flow rate of 1.5 BV/h to perform desorption of the resin.

When measurements show that there was no butanol in the desorption effluent, the remaining desorption solution was emptied from the bed, and 2 BV water was passed through the L-15 resin fixed bed at a flow rate of 0.6 BV/h.

According to the operation of Example 3, the amount of butanol in the desorption effluent was detected by GC, it is obtained through calculation that the desorption rate of butanol in the L-15 resin is 99.2%.

Example 11

At 30° C., 2 BV ethyl acetate was passed through 50 g L-15 resin fixed bed with saturated adsorption of butanol fermentation broth at a flow rate of 0.8 BV/h to perform desorption of the resin.

When measurements show that there was no butanol in the desorption effluent, the remaining desorption solution was emptied from the bed, and 2 BV water was passed through the L-15 resin fixed bed at a flow rate of 0.6 BV/h.

According to the operation of Example 3, the amount of butanol in the desorption effluent was detected by GC, it is obtained through calculation that the desorption rate of butanol in the L-15 resin is 99.1%.

Example 12

At 30° C., 2 BV acetone was passed through 50 g L-15 resin fixed bed with saturated adsorption of butanol fermentation broth at a flow rate of 1 BV/h to perform desorption of the resin.

When measurements show that there was no butanol in the desorption effluent, the remaining desorption solution was emptied from the bed, and 2 BV water was passed through the L-15 resin fixed bed at a flow rate of 0.6 BV/h.

According to the operation of Example 3, the amount of butanol in the desorption effluent was detected by GC, it is obtained through calculation that the desorption rate of butanol in the L-15 resin is 99.1%.

Example 13

At 25° C., 3 BV ethyl ether was passed through 50 g L-15 resin fixed bed with saturated adsorption of butanol fermentation broth at a flow rate of 1.2 BV/h to perform desorption of the resin.

When measurements show that there was no butanol in the desorption effluent, the remaining desorption solution was emptied from the bed, and 2 BV water was passed through the L-15 resin fixed bed at a flow rate of 0.6 BV/h.

According to the operation of Example 3, the amount of butanol in the desorption effluent was detected by GC, it is obtained through calculation that the desorption rate of butanol in the L-15 resin is 99.0%.

Example 14

At 30° C., 2 BV ethyl benzene was passed through 50 g L-15 resin fixed bed with saturated adsorption of butanol fermentation broth at a flow rate of 0.8 BV/h to perform desorption of the resin.

When measurements show that there was no butanol in the desorption effluent, the remaining desorption solution was emptied from the bed, and 2 BV water was passed through the L-15 resin fixed bed at a flow rate of 0.6 BV/h.

According to the operation of Example 3, the amount of butanol in the desorption effluent was detected by GC, it is obtained through calculation that the desorption rate of butanol in the L-15 resin is 99.3%.

Example 15

50 g L-15 resin was made to adsorb butanol fermentation broth to achieve saturation using the adsorption-desorption apparatus shown in FIG. 2 according to the operation of Example 3, and the saturated adsorption capacity of the resin is 120 mg/g.

At 30° C., 2 BV methanol aqueous solution (85% V/V) was passed through the L-15 resin fixed bed with saturated adsorption of butanol fermentation broth at a flow rate of 1 BV/h to perform desorption of the resin.

When measurements show that there was no butanol in the desorption effluent, the remaining desorption solution was emptied from the bed, and 2 BV water was passed through the L-15 resin fixed bed at a flow rate of 0.6 BV/h.

According to the operation of Example 3, the amount of butanol in the desorption effluent was detected by GC, it is obtained through calculation that the desorption rate of butanol in the L-15 resin is 99.6%.

The above adsorption-desorption-regeneration operation was cycled 30 times using the adsorption-desorption apparatus (shown in FIG. 3), and the adsorption capacity and desorption rate of the resin were measured, and the measurements show that the adsorption capacity of L-15 resin on butanol is 120 mg/g, which keeps basically unchanged, and the desorption rate of each operation is higher than 99.3%.

Example 16

At 20° C., 3 BV methanol was successively passed through four fixed bed columns connected in series which were respectively filled with 50 g L-15 resin achieving saturated adsorption of butanol fermentation broth at a flow rate of 0.5 BV/h, to perform desorption of the resin, the effluent after the fourth column was collected and mixed, and then the amount of butanol in the desorption effluent was detected by GC according to the operation of Example 3, it is obtained through calculation that the desorption rate of butanol in the L-15 resin is 99.5%, and the concentration of butanol reaches 81.47 g/L, which is 6.84 times the concentration of butanol in the feed liquid.

When measurements show that there was no butanol in the desorption effluent from the fourth column, the remaining desorption solution was emptied from the bed, and 3 BV water was passed through four L-15 resin fixed bed columns connected in series at a flow rate of 0.6 BV/h to perform desorption of the resin.

What is claimed is:

1. A method for desorbing and regenerating a butanol-adsorbing hydrophobic macroporous polymer adsorbent, the method comprising: successively eluting the hydrophobic macroporous polymer adsorbent with butanol adsorbed therein using a water soluble low-boiling-point polar solvent and water,
wherein the hydrophobic macroporous polymer adsorbent with butanol adsorbed therein adsorbs butanol by adsorbing a butanol fermentation broth.

2. The method for desorbing and regenerating according to claim 1, further comprising: eluting the hydrophobic macroporous polymer adsorbent with water before eluting it with the water soluble low-boiling-point polar solvent,
wherein water for elution is in an amount of 1-2 bed volumes and at a flow rate of 0.5-0.8 bed volumes/hour.

3. The method for desorbing and regenerating according to claim 1, wherein the hydrophobic macroporous polymer adsorbent is a non-polarity and/or weak-polarity hydrophobic macroporous polymer adsorbent.

4. The method for desorbing and regenerating according to claim 3, wherein the inner surface of the hydrophobic macroporous polymer adsorbent is 100-2000 m²/g.

5. The method for desorbing and regenerating according to claim 1, wherein the butanol is n-butanol.

6. The method for desorbing and regenerating according to claim 1, wherein the water soluble low-boiling-point polar solvent is lower alcohol, ketone, ether, ethyl benzene or ethyl acetate, or a mixture of any two or more solvents selected from the group consisting of lower alcohol, ketone, ether, ethyl benzene or ethyl acetate in any proportion, or a mixture of water with any one or more solvents selected from the group consisting of lower alcohol, ketone, ether, ethyl benzene or ethyl acetate in any proportion.

7. The method for desorbing and regenerating according to claim 1, wherein in the method, the hydrophobic macroporous polymer adsorbent is eluted with the water soluble low-boiling-point polar solvent at a flow rate of 0.5-10 bed volumes/hour.

8. The method for desorbing and regenerating according to claim 1, wherein in the method, the hydrophobic macroporous polymer adsorbent is eluted with the water soluble low-boiling-point polar solvent at a temperature of 10-50° C.

9. The method for desorbing and regenerating according to claim 1, wherein in the method, after being eluted with the water soluble low-boiling-point polar solvent, the hydrophobic macroporous polymer adsorbent is eluted with water in amount of 1-2 bed volumes and at a flow rate of 0.5-1 bed volumes/hour.

10. The method for desorbing and regenerating according to claim 2, where the eluting of the hydrophobic macroporous polymer adsorbent with water is performed at 20-25° C.

11. The method for desorbing and regenerating according to claim 3, wherein the non-polarity hydrophobic macroporous polymer adsorbent has a skeleton of styrene diethylbenzene; the weak-polarity hydrophobic macroporous polymer adsorbent has a skeleton of polyacrylamide or styrene diethylbenzene, and has a polar functional group containing nitrogen, oxygen or sulfur.

12. The method for desorbing and regenerating according to claim 3, wherein:
the particle size of the hydrophobic macroporous polymer adsorbent is 20-60 mesh;
the pore diameter of the hydrophobic macroporous polymer adsorbent is 1-180 nm;
the pore volume of the hydrophobic macroporous polymer adsorbent is 0.4-3 cm³/g;
the wet density of the hydrophobic macroporous polymer adsorbent is 590-750 g/L; and
the water content of the hydrophobic macroporous polymer adsorbent is 40-80%.

13. The method for desorbing and regenerating according to claim 6, wherein the water soluble low-boiling-point polar solvent is methanol, ethanol, propanol, acetone, ethyl acetate or ethyl benzene, or a mixture of any two or more solvents selected from the group consisting of methanol, ethanol, propanol, acetone, ethyl acetate or ethyl benzene in any proportion, or a mixture of water with any one or more solvents selected from the group consisting of methanol, ethanol, propanol, acetone, ethyl acetate or ethyl benzene in any proportion.

14. The method for desorbing and regenerating according to claim 1, wherein the hydrophobic macroporous polymer adsorbent is eluted with the water soluble low-boiling-point polar solvent at a flow rate of 0.6-1.5 bed volumes/hour and in amount of 0.5-10 bed volumes.

15. The method for desorbing and regenerating according to claim 1, wherein the hydrophobic macroporous polymer adsorbent is eluted with the water soluble low-boiling-point polar solvent at a temperature of 20-40° C.

* * * * *